(12) United States Patent
Piccone

(10) Patent No.: US 6,871,092 B2
(45) Date of Patent: Mar. 22, 2005

(54) APPARATUS DESIGNED TO MODULATE THE NEUROVEGETATIVE SYSTEM AND INTEGRATE ITS ACTION WITH THAT OF THE CENTRAL NERVOUS SYSTEM; APPLICATIONS IN THE TREATMENT OF THE VASCULAR SYSTEM AND ORTHOPAEDIC DISORDERS

(76) Inventor: Lorenzo Piccone, Via La Pira, 10-Bologna (IT), 40100

( * ) Notice: Subject to any disclaimer, the term of this patent is extended or adjusted under 35 U.S.C. 154(b) by 373 days.

(21) Appl. No.: 10/070,949
(22) PCT Filed: Jul. 27, 2001
(86) PCT No.: PCT/EP01/08756
§ 371 (c)(1),
(2), (4) Date: Mar. 26, 2002
(87) PCT Pub. No.: WO02/09809
PCT Pub. Date: Feb. 7, 2002

(65) Prior Publication Data
US 2002/0165591 A1 Nov. 7, 2002

(30) Foreign Application Priority Data
Jul. 28, 2000 (IT) .................. MI2000A01733

(51) Int. Cl.⁷ ............................... A61N 1/18
(52) U.S. Cl. ............... 607/3; 607/50; 607/72
(58) Field of Search ............... 607/2–5, 46, 48, 607/50, 72

(56) References Cited

U.S. PATENT DOCUMENTS

| | | | |
|---|---|---|---|
| 4,505,275 A | 3/1985 | Chen | 607/62 |
| 5,018,521 A | 5/1991 | Campbell | 607/98 |
| 5,395,398 A | 3/1995 | Rogozinski | 607/50 |
| 5,725,563 A | 3/1998 | Klotz | 607/62 |
| 6,064,911 A | 5/2000 | Wingrove | 607/46 |
| 6,347,247 B1 * | 2/2002 | Dev et al. | 607/2 |
| 6,391,558 B1 * | 5/2002 | Henkens et al. | 435/6 |
| 6,463,323 B1 * | 10/2002 | Conrad-Vlasak et al. | 607/2 |
| 6,678,558 B1 * | 1/2004 | Dimmer et al. | 607/3 |

* cited by examiner

Primary Examiner—Carl Layno
(74) Attorney, Agent, or Firm—Nixon & Vanderhye P.C.

(57) ABSTRACT

This invention relates to a new type of apparatus designed to modulate the neurovegetative system and integrate the neurovegetative action with that of the central nervous system. The method is not invasive, because it uses pulses transmitted through the skin; the intensity of the stimulus is controlled directly by the patient in order to achieve better integration with the central nervous system. This invention effectively treats vascular disorders resulting from obstruction of the arteries of the legs, heart and brain because it induces vasodilatation and increases blood flow and the production of new blood vessels. The method also improves lesions of the spinal column, especially those affecting the back and neck, and other orthopaedic disorders.

18 Claims, 12 Drawing Sheets

APPARATUS DESIGNED TO MODULATE THE NEUROVEGETATIVE SYSTEM AND INTEGRATE ITS ACTION WITH THAT OF THE CENTRAL NERVOUS SYSTEM; APPLICATIONS IN THE TREATMENT OF THE VASCULAR SYSTEM AND ORTHOPAEDIC DISORDERS

This application is the US national phase of international application PCT/EP01/08756 filed 27 Jul. 2001, which designated the US.

FIELD OF THE INVENTION

This invention relates to apparatus and an innovative method designed to regulate the function of the neurovegetative system and integrate it with that of the central nervous system. This effect is achieved by administering electrical pulses to the skin, the intensity of the pulses being controlled directly by the patient.

The new method induces vasodilatation, stimulates neoangiogenesis and increases blood flow. The regulation of the vascular flow obtained with the new technology allows treatment of vascular diseases involving organic obstruction of the arteries, which often affect the lower limbs, heart and brain. The new technology also allows effective treatment of disorders of the spinal column, especially the neck and the lumbosacral area.

The same apparatus can be effectively used to treat many other orthopaedic disorders, for example inflammation and proprioceptive sensory alterations caused by damage to the muscolar and articular system.

BACKGROUND OF THE INVENTION

Atherosclerosis and thrombosis are frequent causes of arterial obstruction.

Atherosclerosis is responsible for most cases of arterial occlusion affecting the myocardium, brain and peripheral arteries.

Arterial obstruction or narrowing causes a reduction in blood flow either during exercise or at rest. The clinical signs result from ischaemia. The atherosclerotic lesions which affect large and small blood vessels in diabetics are very similar to those which appear in non-diabetics; however, they appear earlier, worsen more quickly and are more frequent in the case of diabetics.

Distal arterial occlusion below the knee together with microvascular alterations and neurological lesions are responsible for gangrene. The symptoms are intermittent claudication and pain at rest caused by ischaemia. Diabetic foot, which is caused by a combination of vasculopathy, neuropathy and infection, is one of the most dangerous complications of diabetes, and is the cause of most amputations. Amputation of the foot or leg is five times as frequent in diabetics as in non-diabetics. Angina and myocardial infarction are the most frequent complications of occlusion or stenosis of the coronary artery.

These local actions, together with those of the autonomic nervous system and the vascular system, cause vasoconstriction when activated, such as after exposure to cold; conversely, a reduction in these effects results in vasodilatation.

The development of collateral circulation which results from stenosis or a major obstruction of the arteries influences the degree of ischaemia. Some collateral vessels are present in normal tissue, but do not dilate until arterial obstruction appears, while other capillaries develop in weeks or months. The adrenergic nerves, which are part of the autonomic nervous system, are responsible for vasoconstriction or dilatation of the collateral vessels in response to the increase in arterial pressure, with the result that the flow of blood to the tissue is improved.

Substances produced by the endothelial cells which induce new blood vessel formation (neoangiogenesis) and vasodilatation were recently discovered. The production of VEGF (Vascular Endothelial Growth Factor), which seems to be responsible for the majority of the angiogenic and' vasodilatory effect that results from stenosis or arterial obstruction, appears to be particularly important.

Experiments with isolated animal muscles have demonstrated that continuous electrical stimulation for 5 days (stimulation of 0.3 ms of amplitude, frequency of 150 Hz and voltage of 0.1 V) increases VEGF production, the number of capillaries and the blood flow (Kanno S, Odam Abe M. Circulation 1999; 99, 2682–87).

Although the experiments described above seem to suggest that electrical stimulation of the muscles has beneficial effects on the circulation, the problem remains of how to induce a prolonged stimulation on nerves and muscles in humans.

Patients suffering from acute ischaemia or initial infarction present increased production of VEGF in the myocardium and in the endothelial cells of the capillaries and arterioles (Lee S H, Wolf P L, Escudero R, N. Engi. J. Med. 2000; 342, 626–33).

The revascularisation induced by a transmyocardial laser with the aim of reducing angina pain is accompanied by an increase in VEGF and angiogenesis (Horvath, Chiu E, Maun A C, Annals of Thoracic Surgery 1999; 68, 825–29).

Modern technology offers some highly sophisticated instruments which allow the use of new techniques such as transmyocardial laser revascularisation, but the results are still limited. An electrical phoryngeal neuromuscolar stimulator is disclosed in WO 99/24111.

The treatment of peripheral vascular disease is usually unsatisfactory. Vasodilators have a modest effect, and sympathectomy is ineffective. The injection of VEGF produced by GMO (Genetically Modified Organisms) is not without side effects. The only therapeutic solution is vascular surgery.

In practice, no really effective system for the treatment of peripheral vascular disorders has yet been found. Vasodilators give poor results, treatment with VEGF based on recombinant DNA is not safe enough, and even surgery is just one of the various alternatives, which has not demonstrated any real efficacy.

BRIEF SUMMARY OF THE INVENTION

The present invention proposes an apparatus for the treatment of ischaemic disease which can generate and apply a series of controlled pulses designed to stimulate the patient and elicit an effective response, which eliminates inflammation from the part of the body treated, activates the peripheral microcirculation and stimulates VEGF production.

The apparatus in accordance with the invention uses a non-invasive technique, because the stimulus is transmitted transcutaneously by means of electrodes.

The signals emitted by the machine are sent to the vascular receptors where they induce vasodilatation and stimulate VEGF release.

Using the apparatus in accordance with the invention, ischaemia can be treated and ischaemic pain reduced.

The invention is based on a series of studies conducted by the applicants which demonstrate that by applying a series of electrical pulses to the patient, a biochemical response can be induced which not only eliminates inflammation from the part of the body treated and reduces or eliminates pain, but also has a rapid muscle-relaxant effect, and stimulates vasodilatation and VEGF production.

However, the apparatus must also detect the response of the tissues to electrical stimulation and vary the stimulation parameters to obtain the desired result.

For this purpose, the apparatus to which the invention relates generates electrical pulses whose variables activate the patient's neurophysiological control systems.

The pulse parameters are defined on the basis of the bioreaction of the tissues. The intensity of the pulse is directly regulated by the patient, according to preset treatment programs.

After establishing experimentally that the apparatus in accordance with the invention produces excellent results with muscle relaxation, the inventors formulated the hypothesis that the same apparatus might effectively induce vasodilatation and stimulate VEGF production.

Subsequent experiments demonstrated that this hypothesis was well-founded, and that the apparatus to which the invention relates produces the postulated results.

The apparatus according to the invention comprises:
- means designed to generate electrical pulse series having a width from 10 to 40 $\mu$sec and intensity from 100 to 170 $\mu$Amp, wherein each pulse has a peak that has a width from 7 to 12 nanosec. and a voltage up to 220 Volts;
- means designed to apply the said pulses to a patient through the epidermis;
- means designed to evaluate the tissue reaction;
- means designed to vary the said pulses on the basis of the tissue reaction detected;

at least one of which means can be controlled by the patient/user.

The invention also provides a method of the treatment of vascular and/or muscle and/or tendon disorders, comprising:
a) applying to a patient in need thereof, a series of electrical pulses having a width from 10 to 40 $\mu$sec and intensity from 100 to 170 $\mu$Amp, wherein each pulse has a peak that has a width from 7 to 12 nanosec. and a voltage up to 220 Volts through electrodes located on the epidermis of the area to be treated;
b) detecting the tissue reaction after the application of the pulses;
c) modifying the width and intensity of the pulses in relation to the tissue reaction detected in point b).

The invention also provides a method for increasing the VEGF in a patient in need thereof, comprising:
a) applying to a patient in need thereof, a series of electrical pulses having a width from 10 to 40 $\mu$sec and intensity from 100 to 170 $\mu$Amp, wherein each pulse has a peak that has a width from 7 to 12 nanosec. and a voltage up to 220 Volts through electrodes located on the epidermis of the area to be treated;
b) detecting the tissue reaction after the application of the pulses;
c) modifying the width and intensity of the pulses in relation to the tissue reaction detected in point b).

Advantages features of the apparatus of the invention are stated in the annexed dependent claims.

BRIEF DESCRIPTION OF THE SEVERAL VIEWS OF THE DRAWINGS

One embodiment of the apparatus is illustrated in the attached figures, in which.

DETAILED DESCRIPTION OF THE INVENTION

The circuits illustrated in the figures do not require a more detailed explanation because the information obtainable from the drawings is sufficient to allow an expert in the field to implement the invention.

The apparatus includes devices which generate and regulate a series of electrical pulses that are sent to a pair of electrodes at the output, and is fitted with a control which allows the patient to regulate at least one of the control parameters of the said pulses, especially the voltage, according to preset treatment programs correlating the detected bioreaction to the time, frequency and width of the electrical pulses.

The electrodes, one active and one passive (or reference) electrode, are applied in different positions, depending on the tissue treated.

These regulations can be performed by means of an ordinary control fitted with pushbuttons and/or potentiometers which is activated by the patient.

Figure 1:
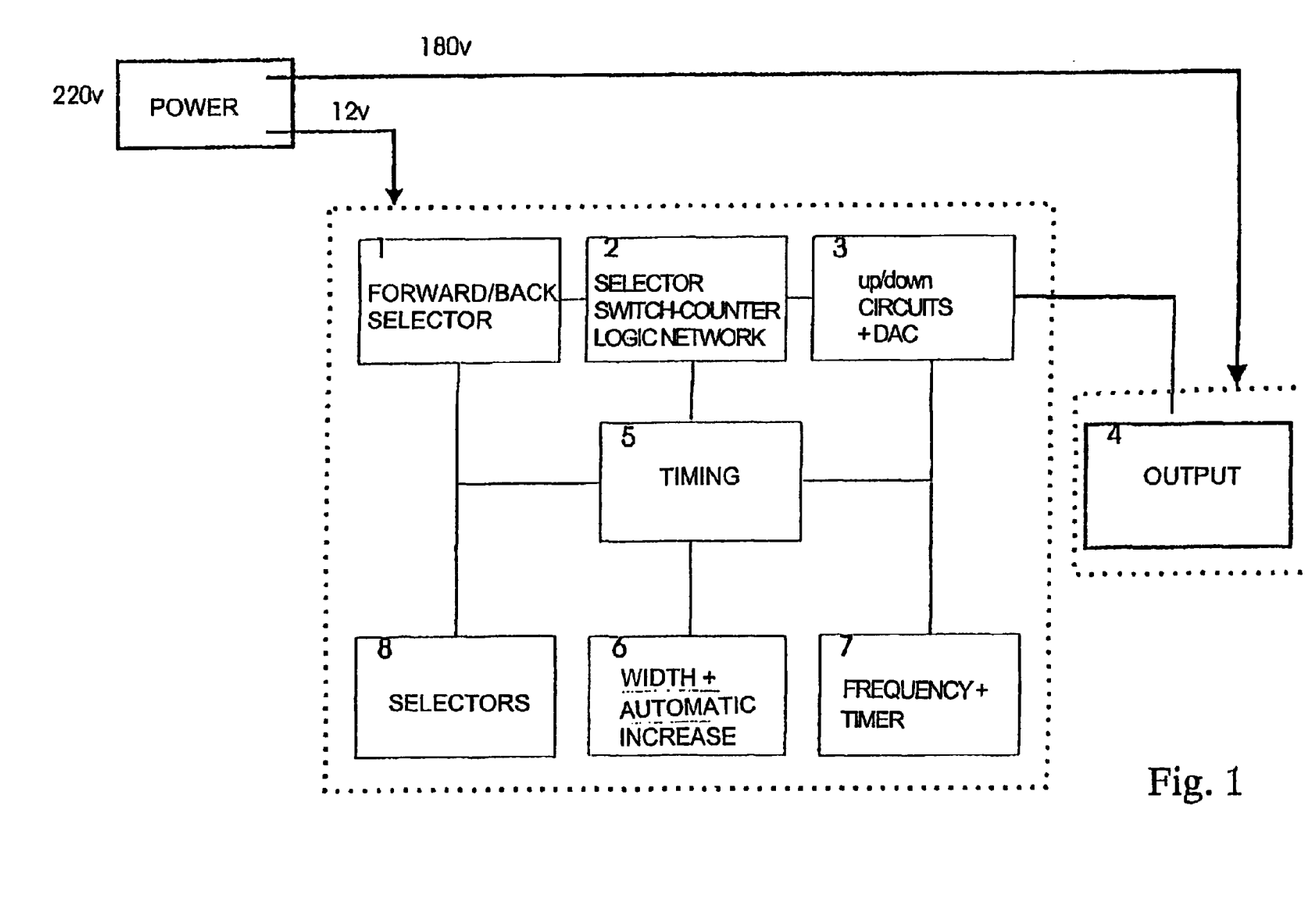
FIG. 1 is a block diagram of the apparatus in accordance with the invention
Figure 2:
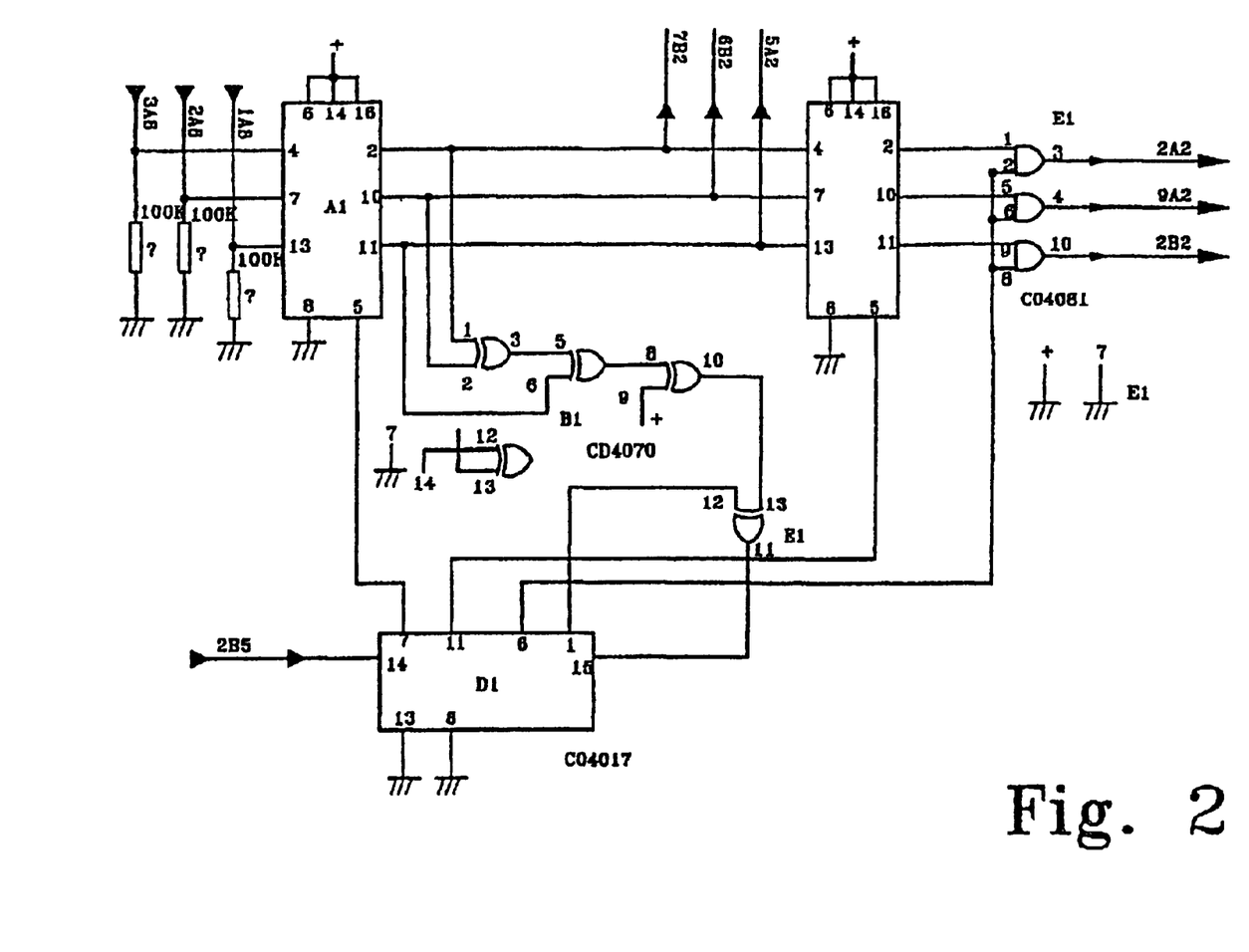
FIG. 2 is the circuit diagram of the forward/back selector switch in the circuit shown in FIG. 1
Figure 3:
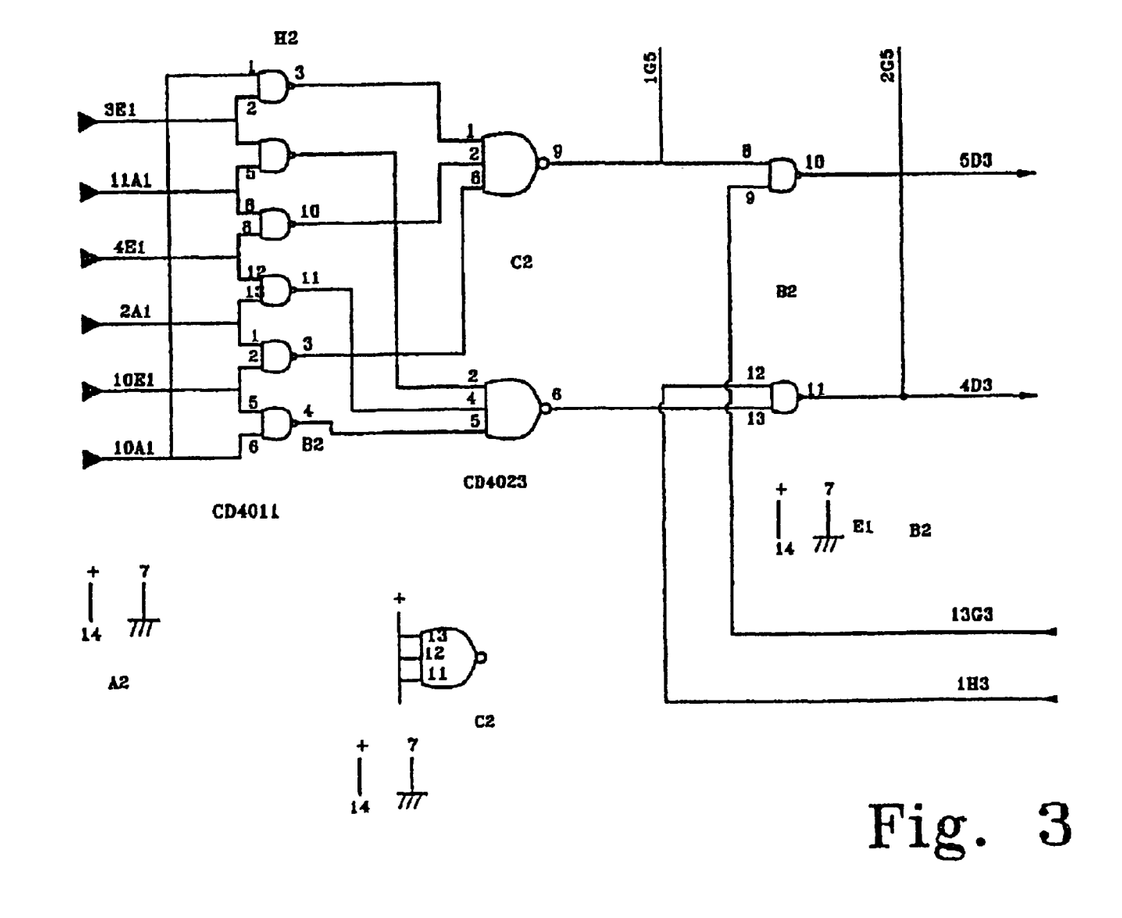
FIG. 3 is the circuit diagram of the selector switch-counter logic network of the circuit shown in FIG. 1

The circuit shown in FIG. 2 allows forward/back regulation, in that it allows the patient to select an increased or reduced voltage, while the circuit shown in FIG. 3 is a counting circuit which counts the number of steps set with the control, in order to calculate the extent of the variation to be imparted to the output voltage signal.

In particular, the amount of this voltage variation is between 0.47 and 0.63 volts.

Figure 4:
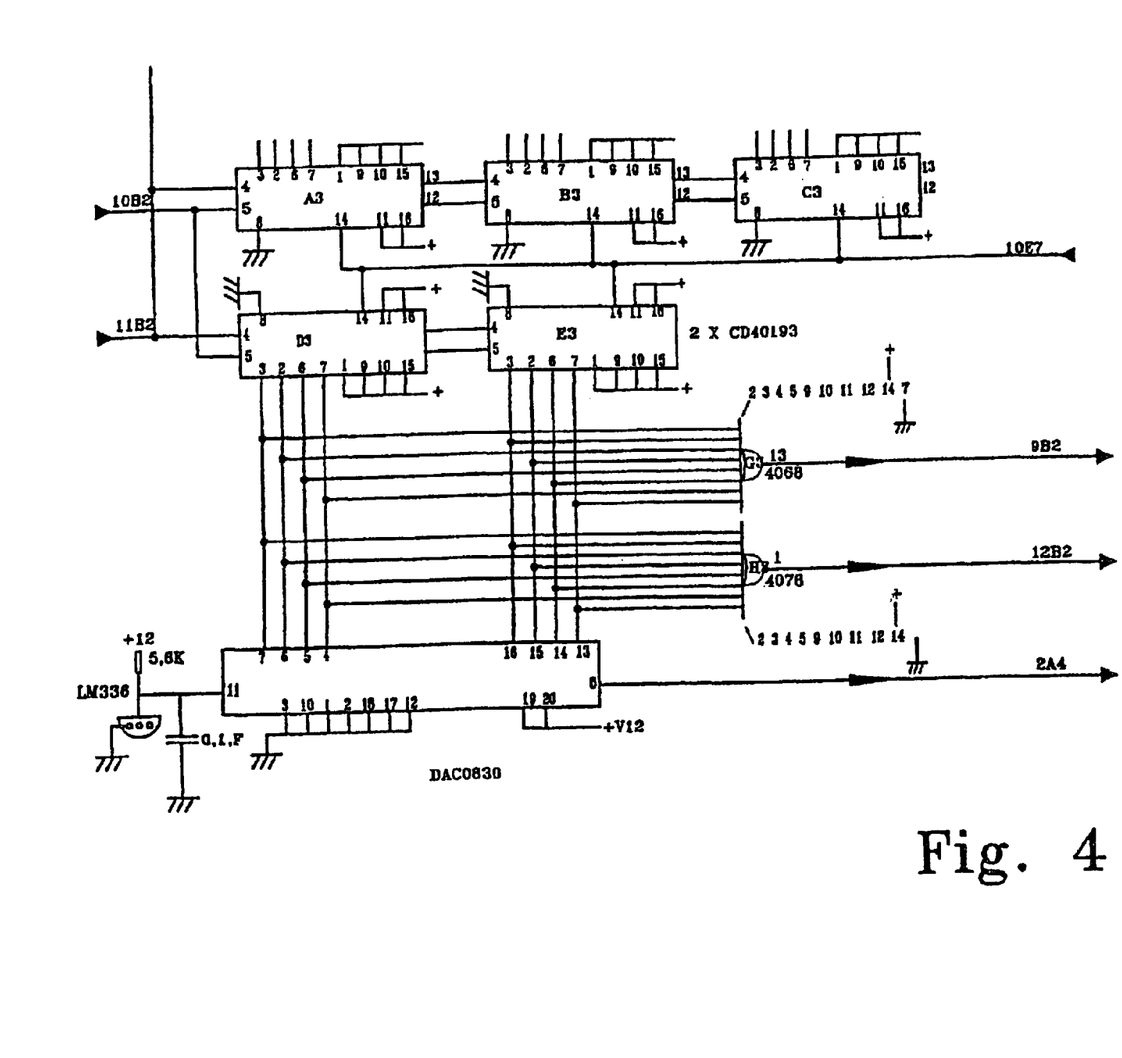
FIG. 4 is a diagram of the up/down circuits, +DAC
Figure 5:
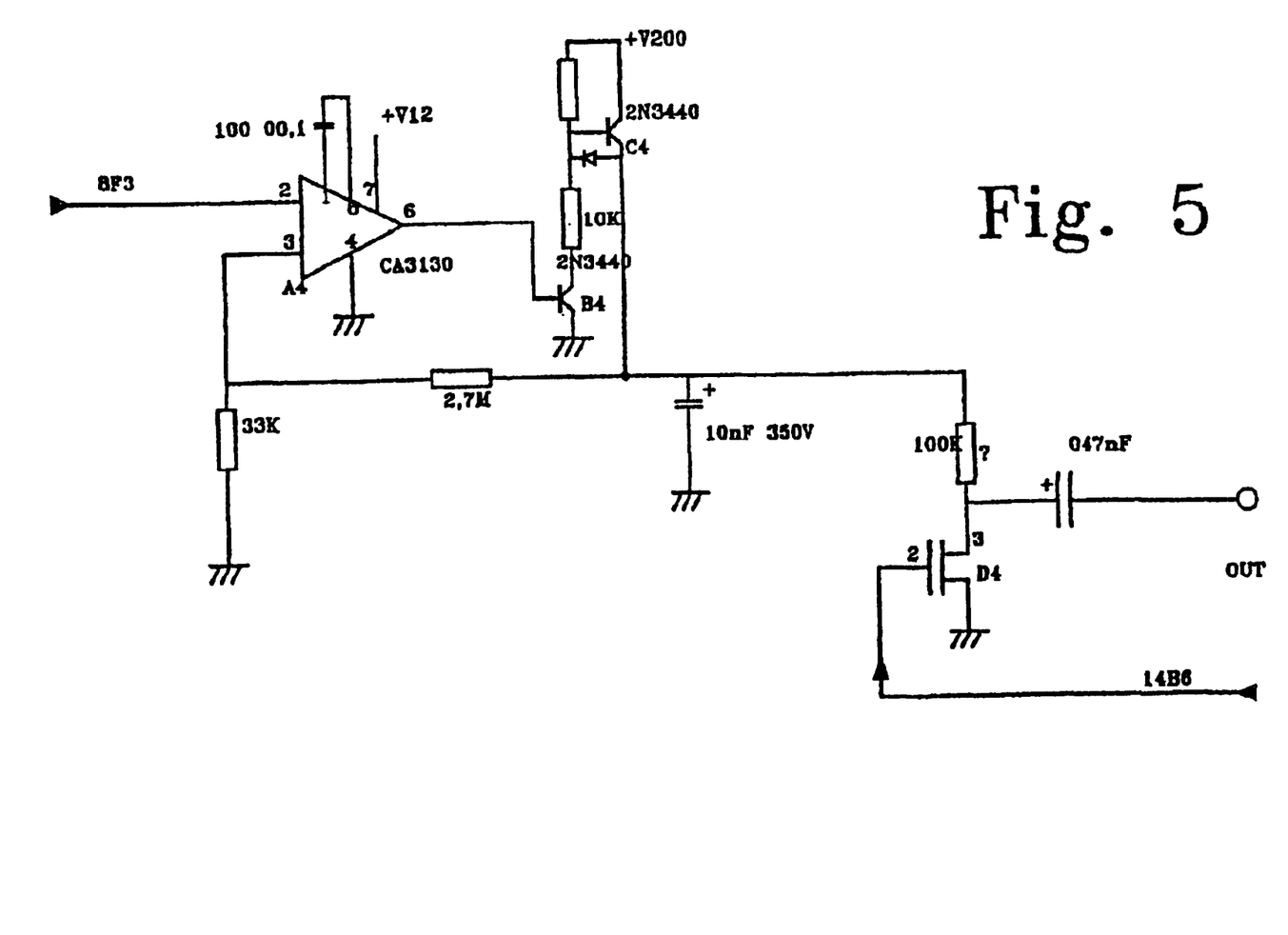
FIG. 5 is the circuit diagram of the output stage of the circuit shown in FIG. 1
Figure 6:
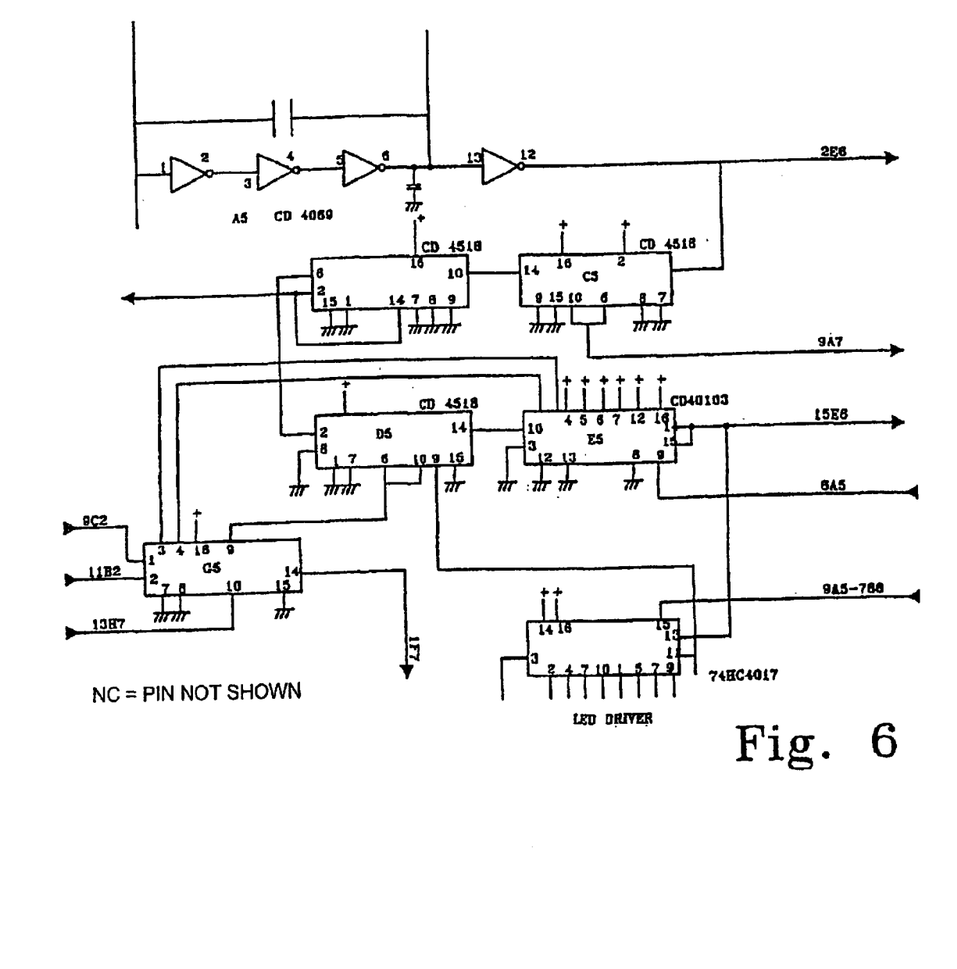
FIG. 6 is the circuit diagram of the timer in the circuit shown in FIG. 1
Figure 7:
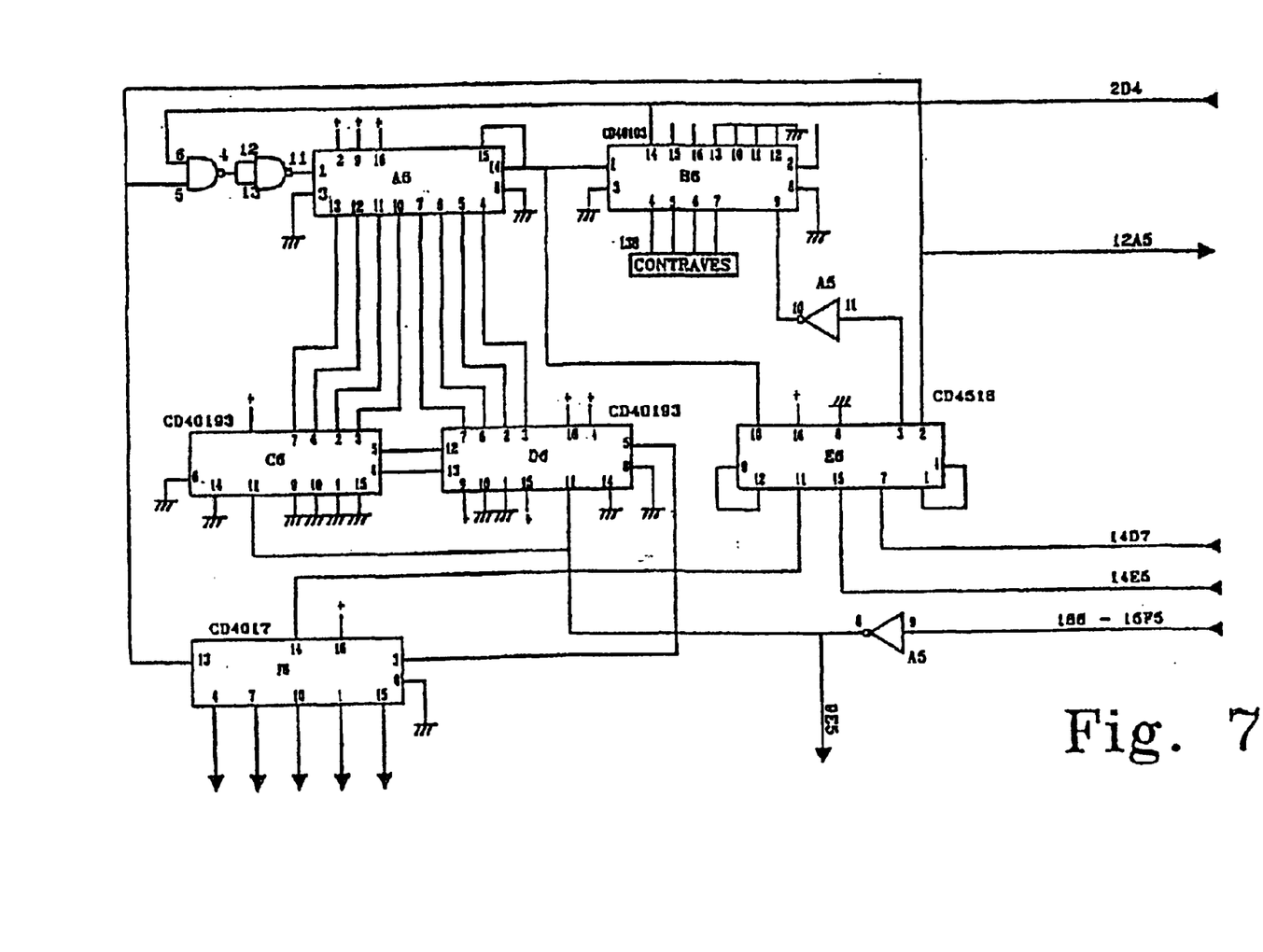
FIG. 7 is the circuit diagram of the automatic pulse train width regulator in the circuit shown in FIG. 1
Figure 8:
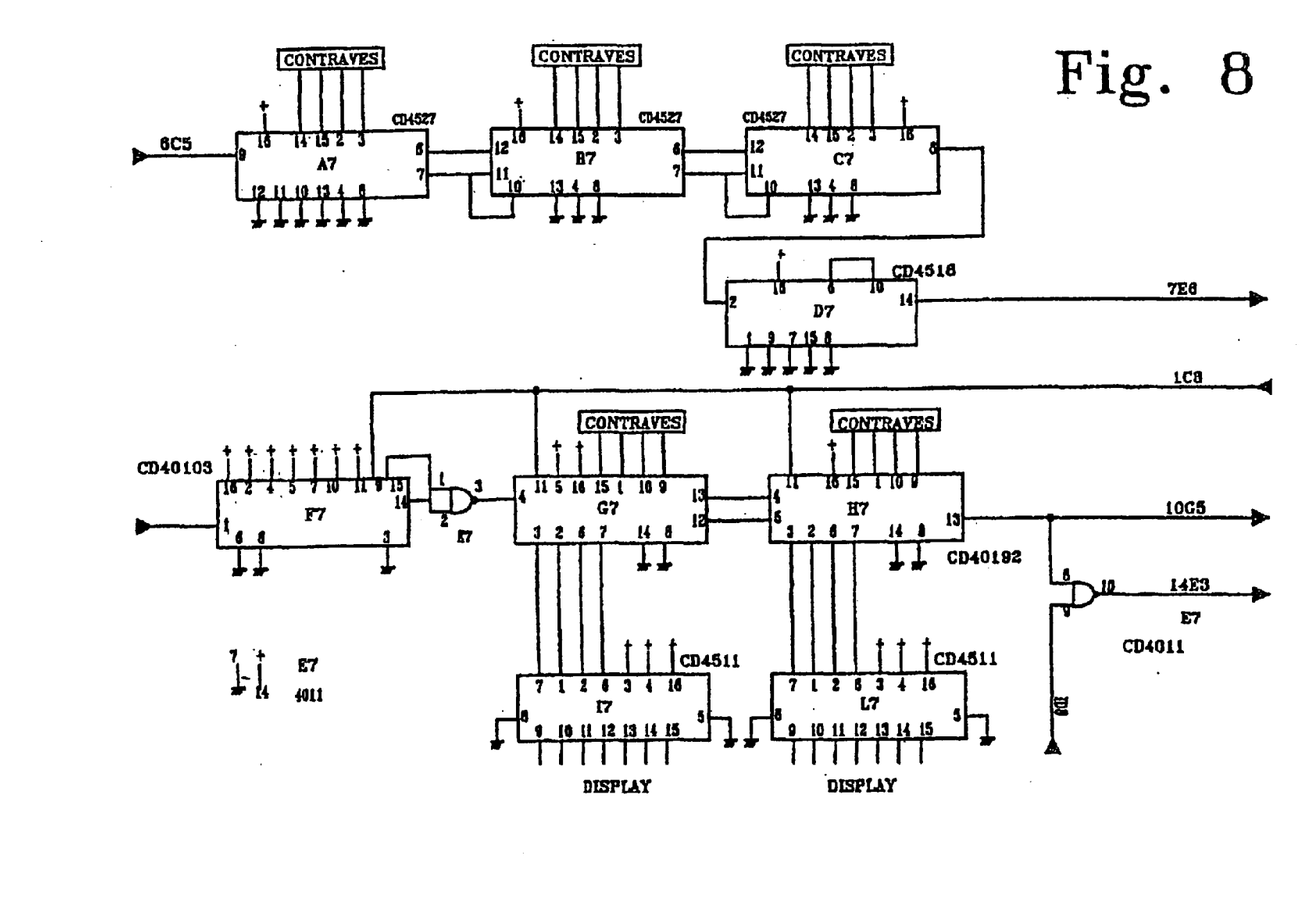
FIG. 8 is the circuit diagram of the frequency regulator and timer in the circuit shown in FIG. 1

The digital count signal output from circuit 3 is then converted into an analog signal in the circuit shown in FIG. 4, where the pulse trains are generated; they then pass to the output stage shown in FIG. 5 after being suitably regulated by the circuits shown in FIGS. 6, 7 and 8.

The circuits shown in FIGS. 6 and 7 regulate the duration (width) of the pulses and the increase in width between two successive pulse trains.

Figure 9:
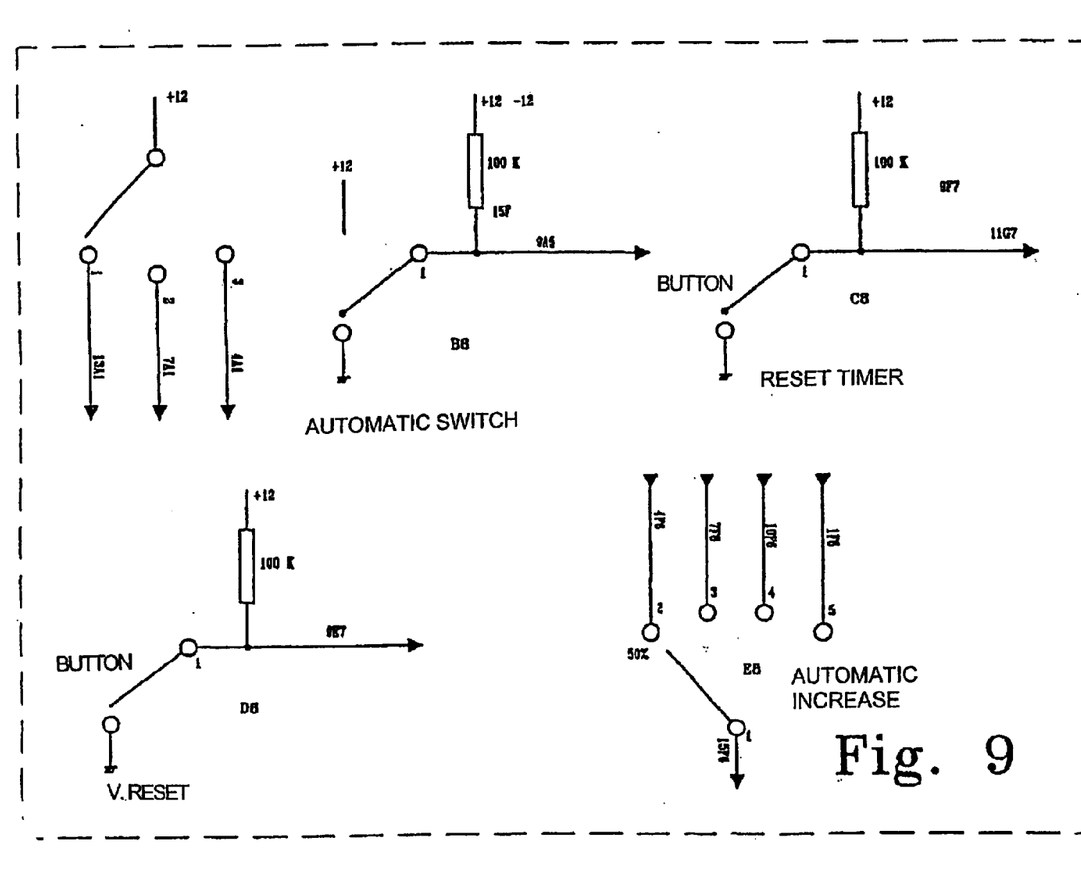
FIG. 9 is the circuit diagram of the control activated by the patient in the circuit shown in FIG. 1.

The circuit shown in FIG. 8 is the timer which determines the duration of the pulse train, while FIG. 9 shows the circuit diagram of the control activated by the patient.

During the initial stage of the experiments, the apparatus was regulated so as to generate a series of pulses with a voltage of approx. 80 volts, the width of each pulse being selectable between 10 and 90 microseconds, and the frequency being selectable between 1 and 999 pulses a second.

The electrodes at the output of the apparatus were applied to the epidermis at the area to be treated, one to the motor point and the other to the muscle belly.

The tests were performed by effecting treatments of different frequencies ranging from 1 to 420 pulses a second, and different widths, ranging from 10 to 50 microseconds, for a total time of 10 to 15 minutes.

120 patients suffering from orthopaedic disorders whose main component was local ischaemia or inflammation were treated.

The results demonstrated good vascularisation of the tissues, but there was no significant improvement in the inflammation.

The pulses were checked with an oscilloscope, which showed that the pulse in contact with the skin underwent considerable deformation, and the patient developed evident tolerance after only 3 minutes.

During a second series of tests, the machine was set to vary the width of the pulses after each series of pulses applied in the same cycle, in order to prevent tolerance by the patient and deformation of the pulses.

300 patients suffering from orthopaedic disorders complicated by inflammation and ischaemia were treated by applying several series of pulses and increasing the pulse width from time to time during the same treatment.

The results demonstrated that reduction of inflammation and improvement in blood flow were associated with modulation of the neurovegetative nervous system.

A further test was then conducted with 120 patients suffering from orthopaedic disorders associated with inflammation or deficiency of the local microcirculation.

The treatment comprised 12 ten-minute sessions in which electrodes were applied to the epidermis at a distance of approx. 10–15 centimetres apart.

The patient could increase or decrease the voltage of the pulse during stimulation with a remote control.

The variation in intensity of the pulse voluntarily decided on by the patient and the variation in the physiological bioreaction time or muscle relaxation times were observed simultaneously with a double-trace oscilloscope.

These first tests confirmed the inventor's intuition, namely that the application of series of electrical pulses under given voltage, frequency and width conditions could produce the desired results.

The following examples and tables show the results of further, more detailed tests.

EXAMPLE 1

Muscle Relaxation (Tables 1a–d and 2)

With the machine in accordance with the invention, one electrode was applied to the motor point and one to the belly of the trapezius muscle, and pulse trains were sent to the patient for 30 seconds at a voltage of approx. 180 volts, with a frequency of one pulse a second and a width of 10 microseconds.

During the second phase, lasting 5 seconds, the pulses were applied at the frequency of one a second, with a width of 20 microseconds.

As the test continued, the parameters were varied from time to time as indicated in the annexed tables 1a to 1d until the muscle reached spasm, then relaxed and remained in that condition.

As will be seen from the graph in Table 2, after approx. 12 phases of treatment the muscle reached an almost permanent state of relaxation.

This relaxation corresponds to the maximum degree of vascularisation and the maximum anti-inflammatory effect.

The anti-inflammatory treatment programme is shown in Table 3 and the associated Graph 4.

Table 5 and the associated graph 6 show a treatment programme for activation of the microcirculation.

The details set out above demonstrate that the apparatus in accordance with the invention is able to relax the muscles, induce vasodilatation, increase the blood flow and stimulate new vessel production.

The technique is non-invasive because the signal is transmitted transcutaneously through electrodes.

The signals emitted with this new technology are conducted by the sensory and proprioceptive fibres of the autonomic nervous system, and reach the vascular and muscle receptors through which vasodilatation and muscle relaxation is produced; the blood flow is increased and VEGF release is stimulated.

The treatment combats ischaemia and reduces pain. The clinical symptoms of ischaemia, such as claudication due to contraction of the calf, thigh or buttocks and pain at rest, rapidly regress, and the patient walks normally.

Vasodilatation and increased blood flow take place in all parts of the body to which the treatment is applied. The effect is long-lasting; however, its duration depends on the degree of arterial obstruction and the time taken for collateral circulation to develop. Measurements taken with a laser doppler demonstrate significant increases in blood flow in the treated areas.

The efficacy of the treatment is demonstrated by the following example.

EXAMPLE 2

12 patients with distal arterial occlusion (7 with occlusion of the tibial artery and 5 with occlusion of the femoral artery) were studied before, during and after stimulation with the new technology.

Figure 10:
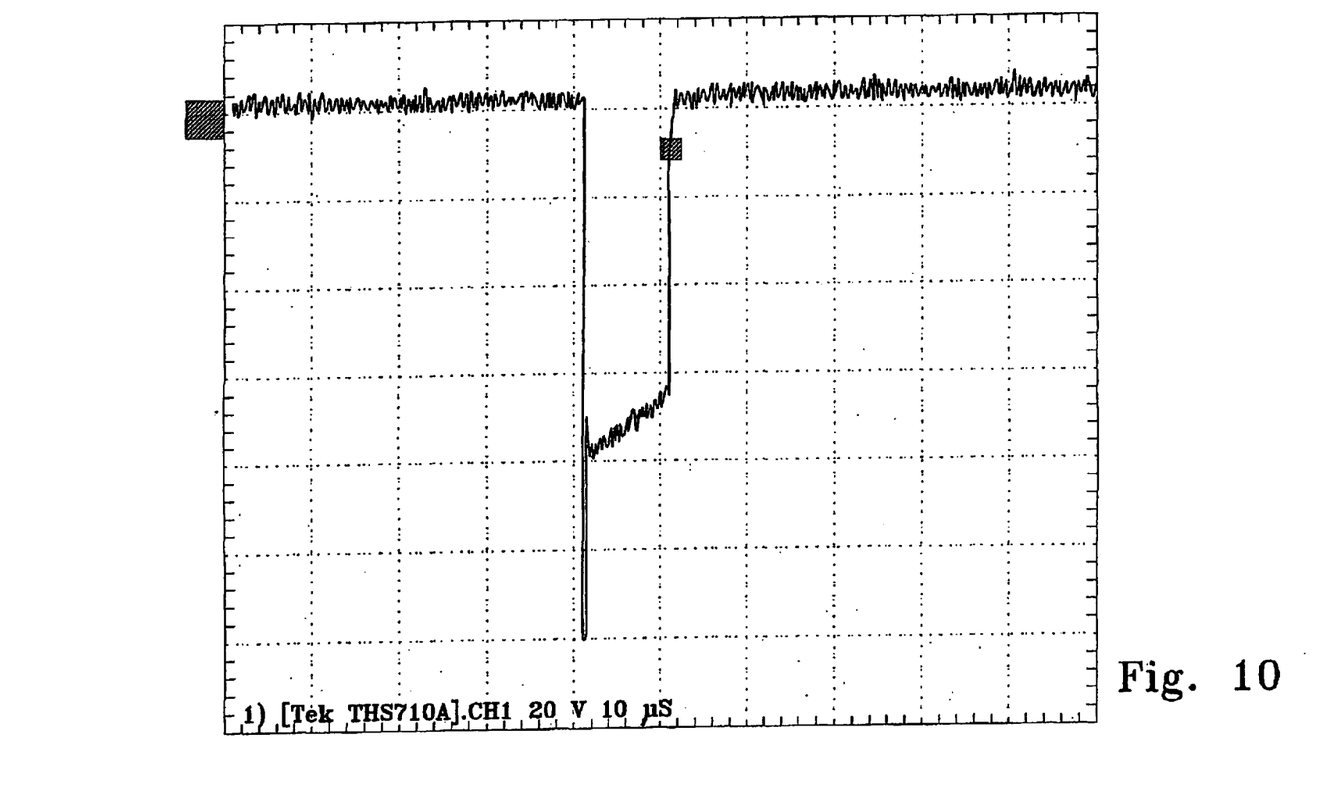
FIG. 10 shows the oscilloscopic trace of a pulse which shows a peak having a width of 10 nanosec.

The VEGF (pg/ml) was assayed at the times shown in FIG. 10.

As will be seen, an increase in VEGF was already evident 2–3 minutes after the start of the stimulus; it peaked after 5 mins (the increase was approx. 50%), and returned to normal after 15 mins.

Further tests confirmed that the best results can be obtained with series of pulses having a width from 10 to 40 $\mu$sec. and an intensity from 100 to 170 $\mu$Amp., with a peak having a width from 7 to 12 nanosec. and a voltage up to 220 Volts.

Figure 11:
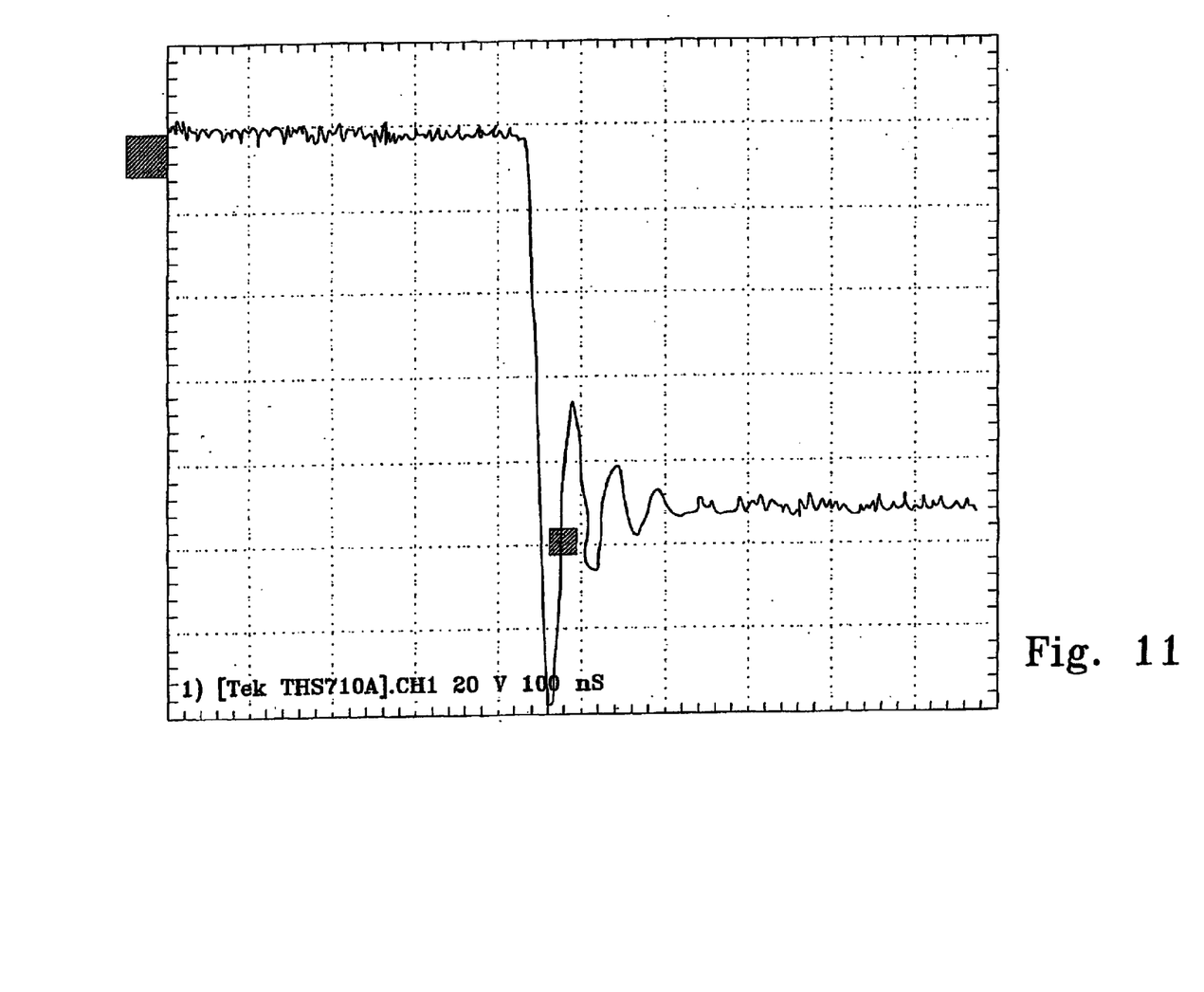
FIG. 11 shows the waveform displayed by an oscilloscope, of the pulse of FIG. 10, over a total time of 100 nanosec.
Figure 12:
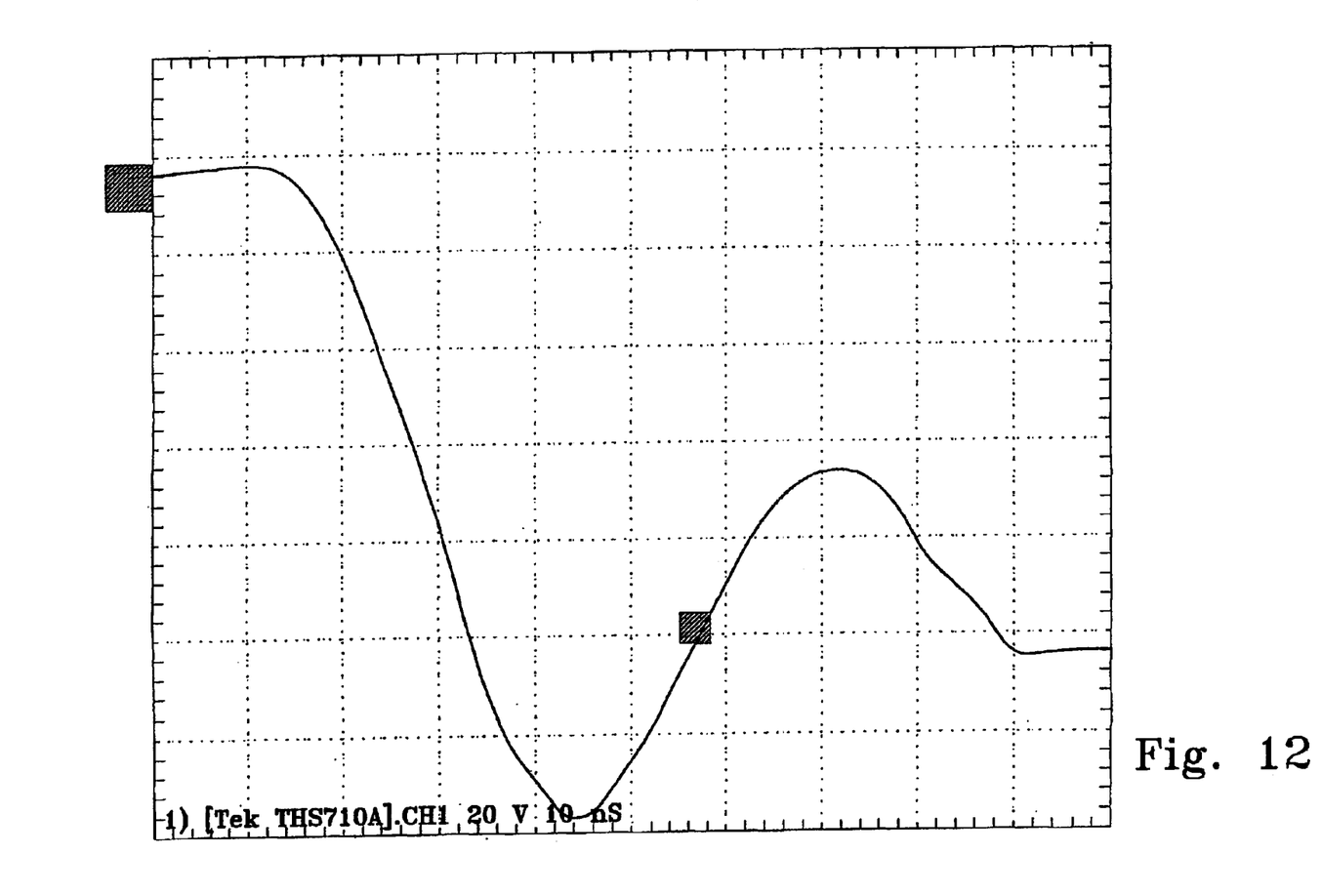
FIG. 12 is an expanded view of the peak of the pulse of FIG. 11.

The waveform of a pulse of this kind, as displayed by an oscilloscope, is shown in FIGS. 10–12.

These data demonstrate for the first time that the application of the invention is able to increase VEGF, the most potent specific endogenous angiogenic factor identified to date. Increased VEGF production was also accompanied by vasodilatation. By contrast with what happens in laboratory animals subjected to a direct stimulus on the isolated muscle and nerve, this method enables the stimulus to be induced through the skin with electrodes. The time taken to stimulate VEGF is a few minutes, whereas the electrical stimulation used in animals takes days to achieve the same result. In the case of severe stenosis or arterial obstruction, recurrence of the ischaemia symptoms after suspension of the treatment is often due to a deficiency in the development of collateral circulation. In this case the treatment must be continued or an arterial bypass performed, which may be followed by new treatment to ensure complete healing of the tissues.

Maintenance of a high blood flow in the treated tissues increases the trophism of the tissue, prevents necrosis and heals ulcers.

The application of this invention to specific parts of the body rather than directly to the heart induces coronary vasodilatation and increases VEGF production in the coronary sinus.

This effect has been observed in 3 patients who underwent cardiac catheterisation, from whom blood samples were taken at the same time to assay the cardiac VEGF.

The treatment can also be applied to lesions of the spinal column and pain syndromes of the back and neck.

The spinal column, together with the spinal cord, nerve roots, spinal ligaments and paraspinal muscles are the sites of some of the most frequent disorders to which human beings are liable. The cervical and lumbar pain which originates in these structures affects nearly everyone sooner or later. This disorder, together with alcoholism, is one of the major causes of absenteeism.

The most important symptom of lesions of the spinal column and the various structures that compose it is pain, which may be local or muscle-related. Pain is caused by irritation of the nerve ending at the site of the pathological process. Treatment of patients with cervical and back pain is very difficult, and often ineffective. Rest, combined with analgesics, is currently considered to be the best treatment. Physiotherapy is performed with the aim of strengthening the paravertebral muscles to prevent painful relapses. Neck manipulation is potentially dangerous. This invention provides an innovative approach to the treatment of lesions of the spinal column.

As mentioned, this new technology acts through the autonomic nervous system, targeting the structures of the spinal column which are most often affected by painful disorders, such as the ligaments, periosteum and paravertebral muscles, by acting on the muscle spindles, the Golgi tendon organs and the joint proprioceptors. Its action is followed by a reduction in oedema, inflammation and pain.

This treatment has been tested on some 200 patients suffering from cervical or lumbar pain.

Most of the patients felt better within a few days (3–10). 60 of them had a slipped disc; 10 of them had already been operated on for slipped disc but still felt pain. The treatment was effective in 92% of cases. 90% of the patients suffering from slipped disc did not need an operation because the compression or inflammation symptoms of the nerve root were eliminated by the treatment.

The results obtained with this method demonstrate that the technique has multiple effects on mechanical lesions of the spinal column and their complications:

it eliminates pain and returns the proprioceptive sensitivity to normal it restores normal muscle contractility it eliminates inflammation.

The same technology has been tested in other disorders.

For example, the invention has been successfully tested in the treatment of numerous other disorders such as cervical, back, hip, thigh and knee pain, knee instability, Achilles tendinitis, calcaneal spur, metatarsalgia, and shoulder, elbow, wrist and hand disorders.

In conclusion, the new treatment improves the quality of life and reduces one of the most frequent causes of absenteeism.

What is claimed:

1. Apparatus for the treatment of vascular and/or muscle and/or tendon disorders and/or to increase the production of Vascular Endothelial Growth Factor (VEGF), and/or for anti-inflammatory treatment and/or for the activation of the microcirculation, comprising:

means designed to generate electrical pulse series having a width from 10 to 40 $\mu$sec and intensity from 100 to 170 $\mu$Amp, wherein each pulse has a peak that has a width from 7 to 12 nanosec. and a voltage up to 220 Volts;

means designed to apply the said pulses to a patient through the epidermis;

means designed to evaluate the tissue reaction;

means designed to vary the said pulses on the basis of the tissue reaction detected;

at least one of which means can be controlled by the patient/user.

2. Apparatus for the treatment of vascular and/or muscle and/or tendon disorders as claimed in claim 1.

3. Apparatus as claimed in claim 1, wherein the voltage of the pulses applied is controlled by the patient/user by suitable means.

4. Apparatus as claimed in claim 1, characterised in that it includes a pair of electrodes designed to transmit the said pulses, one of which can be applied to the motor point and the other to the muscle belly in the area to be treated.

5. Apparatus as claimed in claim 1, characterised in that the said means designed to apply the said pulses include devices able to vary the voltage, amplitude and frequency of the said pulses.

6. Apparatus as claimed in claim 1, characterised in that it includes means designed to regulate the amplitude and frequency of the pulses, which said means are activated directly by the patient.

7. Apparatus for the treatment of muscle contraction as claimed in claim 1, characterised in that it includes a pair of electrodes designed to transmit the said pulses, one of which can be applied to the motor point and the other to the muscle belly in the area to be treated.

8. Apparatus for anti-inflammatory treatment as claimed in claim 1, characterised in that it includes an active electrode designed to be applied at the site of inflammation, and a passive electrode external to the said site.

9. Apparatus for the treatment of vascular disorders as claimed in claim 1, characterised in that it includes an active electrode designed to be applied upstream of the occlusion and a passive electrode designed to be applied downstream thereof.

10. Apparatus for the activation of the microcirculation as claimed in claim 1, characterised in that it includes an active electrode designed to be applied to the ischaemic site and a passive electrode designed to be applied close to the venous plexus.

11. Apparatus as claimed in claim 1, characterised in that it includes means designed to vary the voltage of the pulses applied, with variable increments between 0.47 V and 0.63 V for each step of an up/down circuit which allows the user to select an increased or reduced voltage.

12. Apparatus as claimed in claim 1, characterised in that it includes means designed to vary the number of pulses applied between 1 and 420 pulses/second.

13. Apparatus as claimed in claim 1, characterized in that it includes means designed to vary the width of the pulses between 10 and 50 $\mu$sec.

14. A method of the treatment of vascular and/or muscle and/or tendon disorders, comprising:
   a) applying to a patient in need thereof, a series of electrical pulses having a width from 10 to 40 $\mu$sec and intensity from 100 to 170 $\mu$Amp, wherein each pulse has a peak that has a width from 7 to 12 nanosec. and a voltage up to 220 Volts through electrodes located on the epidermis of the area to be treated;
   b) detecting the tissue reaction after the application of the pulses;
   c) modifying the width and intensity of the pulses in relation to the tissue reaction detected in point b).

15. A method according to claim 14 wherein the pulses are modified according to preset treatment programs correlating the detected bioreaction to the time, frequency and width of the electrical pulses.

16. A method for increasing the Vascular Endothelial Growth Factor (VEGF) in a patient in need thereof, comprising:
   a) applying to a patient in need thereof, a series of electrical pulses having a width from 10 to 40 $\mu$sec and intensity from 100 to 170 $\mu$Amp, wherein each pulse has a peak that has a width from 7 to 12 nanosec. and a voltage up to 220 Volts through electrodes located on the epidermis of the area to be treated;
   b) detecting the tissue reaction after the application of the pulses;
   c) modifying the width and intensity of the pulses in relation to the tissue reaction detected in point b).

17. A method according to claim 16 wherein the patient is affected by a combination of vasculopathy and neuropathy.

18. A method according to claim 17 wherein the patient is affected by diabetic foot.

* * * * *